US00PP20097P3

(12) United States Plant Patent
Bliska et al.

(10) Patent No.: US PP20,097 P3
(45) Date of Patent: Jun. 16, 2009

(54) AMERICAN ELM TREE NAMED 'ST. CROIX'

(50) Latin Name: *Ulmus americana*
Varietal Denomination: St. Croix

(75) Inventors: Christian Bliska, Afton, MN (US); Patricia Bliska, Afton, MN (US); Mark Stennes, New Brighton, MN (US); Chad Giblin, Minneapolis, MN (US)

(73) Assignees: The Elm Tree Farm, LLC, Afton, MN (US); Regents of the University of Minnesota

( * ) Notice: Subject to any disclaimer, the term of this patent is extended or adjusted under 35 U.S.C. 154(b) by 0 days.

(21) Appl. No.: 11/704,772

(22) Filed: Feb. 9, 2007

(65) Prior Publication Data

US 2008/0196132 P1 Aug. 14, 2008

(51) Int. Cl.
*A01H 5/00* (2006.01)

(52) U.S. Cl. ..... Plt./121
(58) Field of Classification Search ..... Plt./221
See application file for complete search history.

(56) References Cited

PUBLICATIONS

*Minnesota Forests*, vol. 8(2): 3–5 (Mar. 2006).

*Primary Examiner*—Annette H Para
(74) *Attorney, Agent, or Firm*—Carol Larcher; Larcher & Chao Law Group

(57) ABSTRACT

A new and distinct variety of American elm tree, particularly distinguished by substantial tolerance to an epiphytotic and normally deadly vascular wilt disease of the genus *Ulmus* known as Dutch elm disease.

4 Drawing Sheets

Latin name *Ulmus americana* L.
Varietal denomination 'St. Croix'.

FIELD OF THE INVENTION

This invention relates to a new and distinct variety or cultivar of the deciduous tree *Ulmus americana,* commonly known as the American elm.

BACKGROUND OF THE INVENTION

This new variety of American elm was discovered in Afton, Minn., on an agricultural property, which was homesteaded in 1855 (U.S. granted title to Thomas Persons) before the tree came into existence.

SUMMARY OF THE INVENTION

This new and distinct variety of American elm is typical of the species as locally represented in every apparent physical way, with the botanical description set forth below. This cultivar is, as typical of the species, vase-shaped, but in this case open-grown and spreading. Color and canopy density are excellent. The species is represented in USDA Hardiness zones 2 through 9 but is restricted to some extent by provenance, meaning seeds from American elm trees growing in Florida are not likely to prosper in Winnipeg, Manitoba. This cultivar is likely to be hardy in USDA hardiness zones 2 through 5 or 6. Given that this mature specimen has survived an unabated Dutch elm disease epidemic for over 30 years without visible injury or infection, while young, wild, American elm trees continue to become infected and die all around it, this cultivar is believed to be exceptionally tolerant to Dutch elm disease.

The tree was asexually reproduced by rooted cuttings and by grafting and budding onto established wild-type and *U. americana* 'Valley Forge' rootstocks. The asexual reproductions ran true to the originally discovered tree from root tip to shoot tip and to each other in all respects.

The asexual reproductions, along with wild-type *U. americana, U. americana* 'Valley Forge' (unpatented). and *U. rubra* elm trees, were inoculated with *Ophiostoma novo-ulmi* (about 0.5 ml of a solution containing $\geqq 10^6$ spores/ml) by means of a hole about ⅛ inch in diameter drilled into the base of the trees, when 3–4 feet in height. The *U. rubra* and *U. americana* 'Valley Forge' and 'St. Croix' became symptomatic, but survived, whereas the wild-type elms wilted and died (R. A. Blanchette, unpublished data).

DETAILED BOTANICAL DESCRIPTION OF THE PLANT

Figure 1:
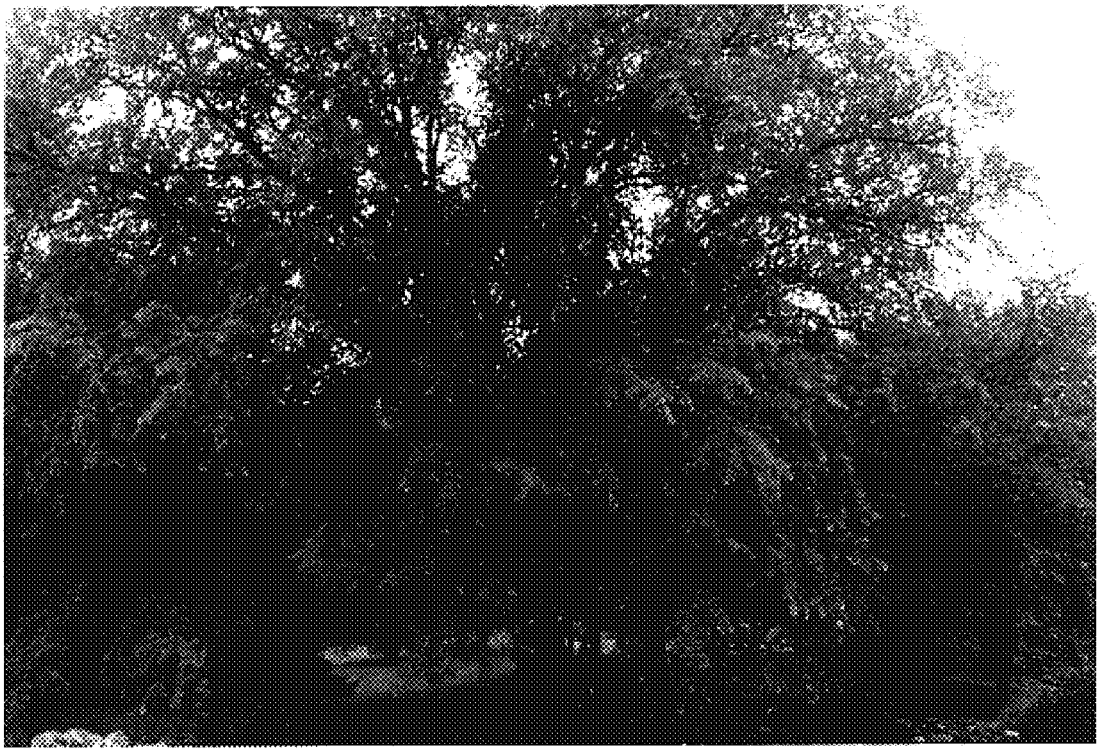
FIG. 1 is a photograph showing the timber form of 'St. Croix.'
Figure 2:
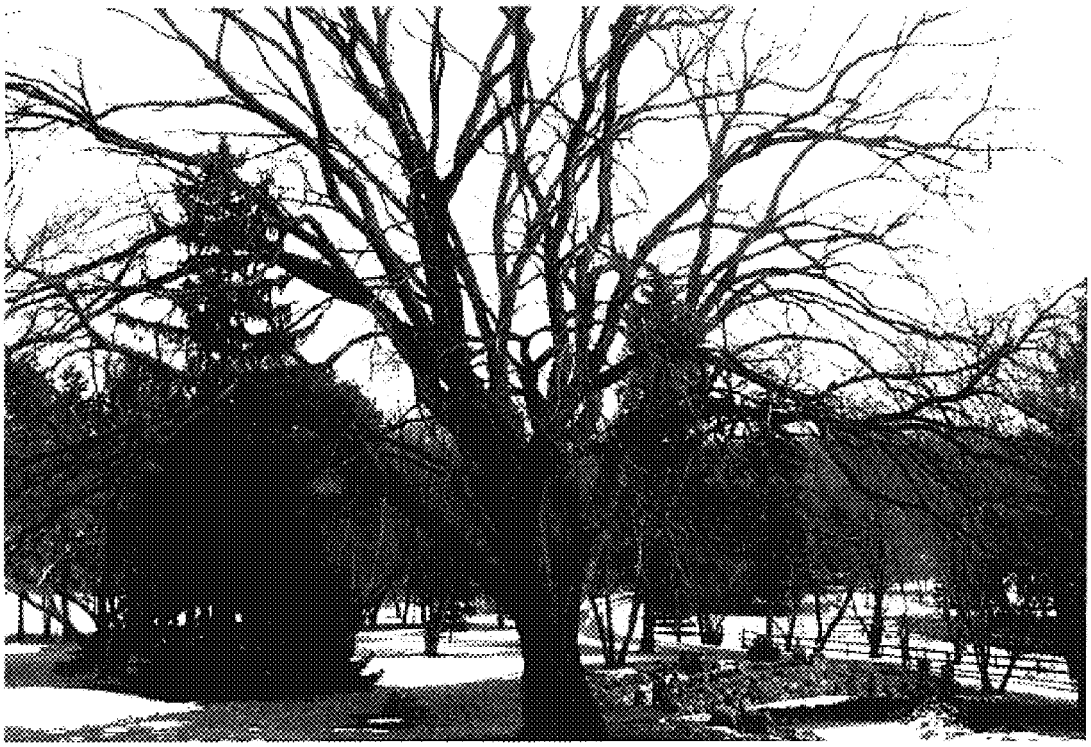
FIG. 2 is a photograph showing the timber form of 'St. Croix' in the absence of leaves.
Figure 3:
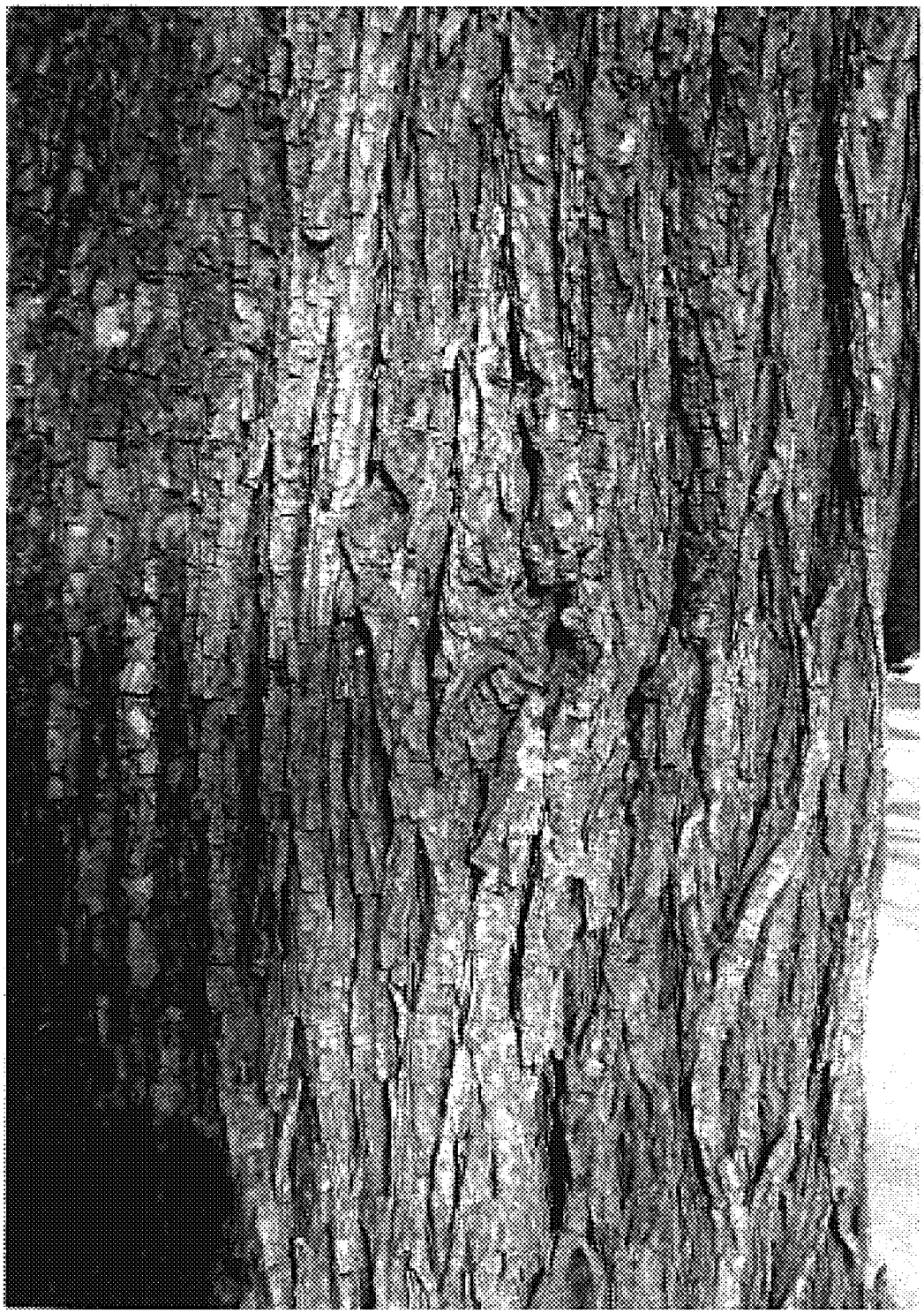
FIG. 3 is a photograph showing the bark of 'St. Croix.'
Figure 4:
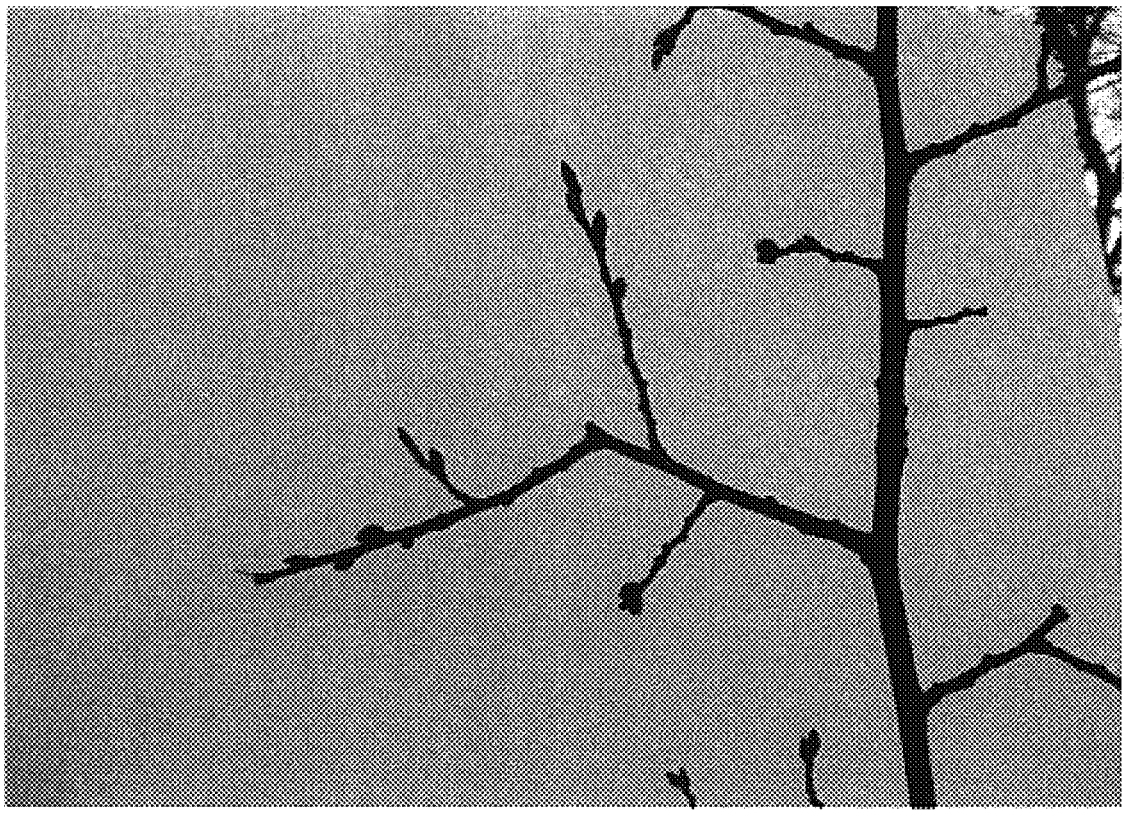
FIG. 4 is a photograph showing the twigs of 'St. Croix.'

The botanical details of this new and distinct variety of American elm tree are as follows:

The 'St. Croix' is an exceptionally large specimen of the American elm species. The diameter at breast height (dbh; ~4.5 feet above the ground) is about 75 inches (19 feet, 8 inches in circumference). It is about 75 feet high with a crown spread of about 110 feet. Its age is unknown, but likely to be between 80 and 110 years. Visually the 'St. Croix' differs from the 'Princeton' in that the 'St. Croix' grows more openly with a spreading canopy, whereas the 'Princeton' grows more vertically erect with narrow branch angles. The 'Valley Forge,' on the other hand, is poorly disciplined in comparison to the 'St Croix' and requires more frequent pruning.

Vigor as a genetic measure of suitability for the site is excellent. The rate of growth can be characterized as medium to fast. Upon cultivation in a nursery, juvenile trees can grow up to about 100 inches per year. A growth rate of 10–15 feet over five years can be common in early maturity.

Hardiness on the USDA hardiness zone map is likely to be in zones 2 through 5 or 6.

General health and pest susceptibility: Vitality as a measure of health is very good, with good canopy density and excellent dark green color. The tree is normally susceptible to extant indigenous pests, all of minor importance.

Growth habit and rate: The 'St. Croix' has an open-grown, spreading, vase-shaped crown. The growth rate is fast and typical of the species in this part of Minnesota.

The color of the bark varies from light brown (99660 on the HTML True Color Chart) to silver-gray (CCCC on the HTLM True Color Chart), depending on whether the bark is on the trunk, the branches (as well as the size of the branches), or in the canopy of the tree. Bark is typically divided into grayish, flat-topped ridges, which are separated by roughly diamond-shaped fissures and which become indefinite in pattern in the canopy. Bark on young branches is smooth with inconspicuous lenticels, which are rod-shaped about 1/16 inch in length, and have a color approximating that of CC9900 on the HTML True Color Chart.

Twigs are slender, zigzag, brown, glabrous or slightly pubescent; lateral buds are about ¼" long, ovoid, acute but not sharp-pointed, smooth or sparingly downy, chestnut brown.

Leaves are deciduous, simple, alternate, short-petioled, 2-ranked, dark green (closest to 006600 on HTML True Color Chart), 4 to 6 inches long, 1 to 3 inches wide and oblong-obovate to elliptical; margin coarsely doubly serrate; apex acuminate; base conspicuously inequilateral; surfaces glabrous (smooth) or slightly scabrous (roughened) above, usually pubescent below; veins alternate, ascending, parallel and extending from central vein to apex of longest serrations.

The petioles are ¼ inch to ⅓ inch long and vary in color from pale, yellow green (CCCC33 on the HTML True Color Chart) to light brown (996600 on the HTML True Color Chart) with age.

Flowers arc vernal appearing before the leaves unfold, perfect, greenish-red (666600 on the HTML True Color Chart), born in long-pedicelled fascicles of 3 or 4; ovary flattened, surmounted by a deeply 2-lobed style.

Fruit is a samara maturing from a greenish color (669900 on the HTML True Color Chart) to a light brown color (996600 on the HTML True Color Chart) in the spring as the leaves unfold; about ½ inch long, oval to oblong-obovate, deeply notched at apex, margin ciliate with smooth surfaces.

We claim:

1. A new and distinct variety of American elm tree named 'St. Croix' substantially as illustrated and described.

* * * * *